(12) United States Patent  
Samaritani et al.

(10) Patent No.: US 7,740,884 B2  
(45) Date of Patent: Jun. 22, 2010

(54) FREEZE-DRIED FSH/LH FORMULATIONS

(75) Inventors: Fabrizio Samaritani, Rome (IT); Piergiorgio Donati, Morges (CH)

(73) Assignee: Ares Trading S.A., Aubonne (CH)

( * ) Notice: Subject to any disclaimer, the term of this patent is extended or adjusted under 35 U.S.C. 154(b) by 563 days.

(21) Appl. No.: 10/561,529

(22) PCT Filed: Jun. 16, 2004

(86) PCT No.: PCT/EP2004/051138

§ 371 (c)(1),
(2), (4) Date: May 30, 2006

(87) PCT Pub. No.: WO2004/112826

PCT Pub. Date: Dec. 29, 2004

(65) Prior Publication Data

US 2007/0059252 A1    Mar. 15, 2007

(30) Foreign Application Priority Data

Jun. 20, 2003 (EP) .................................. 03101830

(51) Int. Cl.
*A61K 9/14* (2006.01)
*A61K 38/24* (2006.01)
*A61K 38/16* (2006.01)
*A61K 31/70* (2006.01)

(52) U.S. Cl. ............................. 424/499; 514/2; 514/8; 514/23; 424/198.1; 530/313

(58) Field of Classification Search ........................ None
See application file for complete search history.

(56) References Cited

U.S. PATENT DOCUMENTS

| | | | |
|---|---|---|---|
| 4,496,537 A | 1/1985 | Kwan | |
| 4,589,402 A | 5/1986 | Hodgen et al. | |
| 4,659,696 A | 4/1987 | Hirai et al. | |
| 4,670,419 A | 6/1987 | Uda et al. | |
| 4,746,508 A | 5/1988 | Carey et al. | |
| 4,962,091 A | 10/1990 | Eppstein et al. | |
| 5,087,615 A | 2/1992 | Chappel | |
| 5,128,453 A | 7/1992 | Arpaia et al. | |
| 5,162,306 A | 11/1992 | Donaldson | |
| 5,270,057 A | 12/1993 | de Meere et al. | |
| 5,356,876 A | 10/1994 | Espey | |
| 5,374,620 A | 12/1994 | Clark et al. | |
| 5,384,132 A | 1/1995 | De Meere et al. | |
| 5,508,261 A | 4/1996 | Moyle et al. | |
| 5,580,856 A | 12/1996 | Prestrelski et al. | |
| 5,639,640 A | 6/1997 | Reddy et al. | |
| 5,650,390 A | 7/1997 | Samaritani et al. | |
| 5,661,125 A | 8/1997 | Strickland | |
| 5,681,822 A | 10/1997 | Bornstein et al. | |
| 5,733,572 A | 3/1998 | Unger et al. | |
| 5,767,067 A | 6/1998 | Arpaia et al. | |
| 5,811,096 A | 9/1998 | Aleman et al. | |
| 5,889,110 A | 3/1999 | Hutchinson et al. | |
| 5,929,028 A | 7/1999 | Skrabanja et al. | |
| 5,945,187 A | 8/1999 | Buch-Rasmussen et al. | |
| 6,066,620 A | 5/2000 | McGregor et al. | |
| 6,136,784 A | 10/2000 | L'Italien et al. | |
| 6,238,890 B1 | 5/2001 | Boime et al. | |
| 6,267,958 B1 | 7/2001 | Andya et al. | |
| 6,440,930 B1 | 8/2002 | Rinella, Jr. | |
| 6,541,606 B2 | 4/2003 | Margolin et al. | |
| 6,573,237 B2 | 6/2003 | Rinella, Jr. | |
| 2003/0072803 A1 | 4/2003 | Goldenberg et al. | |
| 2006/0241047 A1 | 10/2006 | Hoffmann et al. | |

FOREIGN PATENT DOCUMENTS

| | | |
|---|---|---|
| CA | 1340132 | 11/1998 |
| DE | 41 17 078 A1 | 11/1882 |
| EP | 0 318 081 | 5/1989 |
| EP | 0 448 146 | 9/1991 |
| EP | 0 652 766 | 7/1993 |
| EP | 0 603 159 | 6/1994 |
| EP | 0 853 945 | 7/1998 |
| EP | 0 920 873 | 12/1998 |
| EP | 0 891 774 | 1/1999 |
| EP | 0 668 073 | 4/1999 |
| EP | 1 191 099 | 6/1999 |
| EP | 0 736 303 | 8/1999 |
| EP | 0 974 359 | 1/2000 |
| EP | 1176976 | 7/2006 |
| FR | 2782455 | 2/2000 |
| GB | 839300 | 8/1958 |

(Continued)

OTHER PUBLICATIONS

Observations by a third party concerning the patentability of the invention of EP application No. 04766052.7-2107 (EP1176976) dated Jan. 28, 2008.
Akers Michael J., "Considerations in selecting antimicrobial preservative agents for parenteral product development", Pharmaceutical Technology, May 1984, pp. 36-46.
Akers, Michael J., "Excipient—Drug Interactions in Parenteral Formulations", Journal of Pharmaceutical Sciences, Nov. 2002, vol. 91, No. 11, pp. 2283-2300.
Amir, Syed M. et al., "Phenol, A Potent Stimulator of Adenylate Cyclase in Human Thyroid Membranes", Endocrine Research Communications, 8(2):83-95, 1981.
A.P.L.® Injection 5 000 IU and Injection 10 000 IU, http://home.intekom.com/pharm/akromed/apl-inj.html, Dec. 12, 2002, pp. 1-2.
Arzneiformenlehre, Paul Heinz List, Wissenschaftliche Verlagsgellschaft mbH, Stuttgart, 4th Edition, 1985, pp. 402-407.
Boime, Irving et al., "Glycoprotein Hormone Structure-Function and Analog Design", Recent Progress in Hormone Research, vol. 54, 1999, The Endocrine Society, pp. 271-289.

(Continued)

*Primary Examiner*—Lorraine Spector
*Assistant Examiner*—Elly-Gerald Stoica
(74) *Attorney, Agent, or Firm*—Woodard, Emhardt, Moriarty, McNett & Henry LLP

(57) ABSTRACT

The invention relates to the field of pharmaceutical formulations of a mixture of follicle stimulating hormone (FSH) and luteinising hormone (LH), and to methods of producing such formulations.

12 Claims, No Drawings

FOREIGN PATENT DOCUMENTS

| GB | 1065127 | 4/1967 |
|---|---|---|
| WO | WO 92/21332 | 12/1992 |
| WO | WO 92/22568 | 12/1992 |
| WO | WO 93/11788 | 6/1993 |
| WO | WO 94/03198 | 2/1994 |
| WO | WO 97/04801 | 2/1997 |
| WO | WO 97/17087 | 5/1997 |
| WO | WO 98/30592 | 7/1998 |
| WO | WO 99/21534 | 5/1999 |
| WO | WO/00/67778 | * 11/2000 |

OTHER PUBLICATIONS

Combarnous, Yves, "Molecular Basis of the Specificity of Binding of Glycoprotein Hormones to Their Receptors", Endocrine Reviews, 1992. vol. 13, No. 4, pp. 670-691.

CPMP Guidelines antimicrobial preservative inclusion, CPMP/CVMP/OWP/115/95, Jul. 8, 1997, pp. 1-6.

de Medeiros, S.F. et al., "Stability of Immunoreative β-Core Fragment of hCG", Obstetrics & Gynecology, vol. 77, No. 1, Jan. 1991, pp. 53-59.

Fransson, Jonas et al., "Solvent Effects on the Solubility and Physical Stability of Human Insulin-Like Growth Factor 1", Pharmaceutical Research 14(5):606-12, 1997.

Frenken, L.A.M. et al., "Analysis of the Efficacy of Measures to Reduce Pain After Subcutaneous Administration of Epoetin Alfa", Nephrology Dialysis Transplantation 9:1295-98, 1994.

Furuhashi, M. et al. "Fusing the Carboxy-Terminal Peptide of the Chorionic Gonadotropin (CG) beta Subunit to the Common alpha-Subunit: Retention of O-linked Glycosylation and Enhanced in Vivo Bioactivity of Chimeric Human CG", Molecular Endocrinology, 1995, vol. 9, No. 1, pp. 54-63.

Garcia-Campayo, Vincenta et al., "Design of Stable Biologically Active Recombinant Lutropin Analogs", Nature Biotechnology 15:663-67, 1997.

Gennaro et al., "Parenteral Preparations", Chapter 84, Remington's Pharmaceutical Sciences (18th Edition, Mack Publishing. Co., 1990, see part 8 "Pharmaceutical Preparations and their Manufacture," pp. 1545-1569.

Gonal-F® (follitropin alfa for injection) For subcutaneous injection: Package Insert Code N1900101B, manufactured by Serono Laboratories, Inc., Randolph, MA, USA, published Sep. 1997.

Harvey, Stewart C., "Antiseptics and Disinfectants; Fungicides; Ectoparasiticides", The Pharmacological Basis of Therapeutics, 6th Edition, Chapter 41, 964-987, 1980.

Heikoop, Judith C. et al., "Structure-based design and protein engineering of intersubunit disulfide bonds in gonadotropins" Nature Biotechnology, Jul. 1997, vol. 15, pp. 658-662.

Package insert HRF, "HRF* Injection 0,1 mg and HRF* Injection 0,5 mg", Malahyde Information Systems, 2003, pp. 1-4.

Jorgenson, Jan Trost, "Improvement of Patient Convenience in Treatment with Growth Hormone", Journal of Pediatric Endocrinology, 1994, 7(2):175-180.

Kesner, J.S. et al., "Stability of Urinary Female Reproductive Hormones Stored Under Various Conditions", Reproductive Toxicology, vol. 9, No. 3, pp. 239-244, 1995.

Lam, Xanthe M. et al., "The Effect of Benzyl Alcohol on Recombinant Human Interferon-γ" Pharmaceutical Research, 1997, vol. 14, No. 6, 725-729.

Leukine Package Insert/Approved Text, Rev. 0230-02, Issued Feb. 1998, pp. 1-30.

Livesey J. H. et al., "Glycerol prevents loss of immunoreactive follicle-stimulating hormone and luteinizing hormone from frozen urine", Journal of Endocrinology, vol. 98, pp. 381-384, 1983.

Livesey, J. H. et al., "Effect of Time, Temperature and Freezing on the Stability of Immunoreative LH, FSH, TSH, Growth Hormone, Prolactin and Insulin in Plasma", The Medical Unit, Princess Margaret Hospital, Christchurch 2, New Zealand, Jun. 25, 1980, Biochem 13 (4), 1980, pp. 151-155.

Maa, Yuh-Fun, et al., "Aggregation of recombinant human growth hormone induced by phenolic compounds", International Journal of Pharmaceutics, 1996, vol. 140, pp. 155-168.

Pimpalkhute, M. et al., "Radioimmunoassay of Human Follicle Stimulating Hormone/HFSH/", J. Radioanal. Nucl. Chem. Letters, 1986, 103, No. 2, pp. 105-116.

Pregnyl Prescribing Information, Pregnyl (chorionic gonadotropin for injection, USP), Organon Inc., Aug. 1998, pp. 1-4.

Profasi (chorionic gonadotropin for injection, USP) for intramuscular injection, Serono Laboratories, Inc. (revised Jun. 1993).

Rafferty, M.J. et al., "Safety and Tolerability of a Multidose Formulation of Epoetin Beta in Dialysis Patients", Clinical Nephrology. 54(3):240-45, 2000.

Remmele Jr., Richard L. et al., "Interleukin-1 Receptor (IL-1R) Liquid Formulation Development Using Differential Scanning Calorimetry", Pharmaceutical Research, 1998, vol. 15, No. 2 pp. 200-208.

Rose, M.P. et al, "Characterisation, calibration and comparison by international collaborative study of international standards for the calibration of therapeutic preparations of FSH", Journal of Endocrinology, vol. 158, pp. 97-114, 1998.

St. Peter, Wendy L. et al., "Pain Comparison After Subcutaneous Administration of Single-Dose Formulation Versus Multidose Formulation of Epogen in Hemodialysis Patients", American Journal of Kidney Diseases, 32(3):470-74, 1998.

Saketos, Maria et al., "Time-Resolved Immunofluorometric Assay and Specimen Storage Conditions for Measuring Urinary Gonadotropins", Clinical Chemistry, vol. 40, No. 5, 1974, pp. 749-753.

Saxena, B.B. et al., "Amino Acid Sequence of the β Subunit of Follicle-stimulating Hormone from Human Pituitary Glands", The Journal of Biological Chemistry, vol. 251, No. 4, pp. 993-1005, Feb. 25, 1976.

Serono Study Report GF 9873, "Evaluation of FSH Formulations claimed in EP-974'359", dated Mar. 22, 2004.

Shome, B. et al., "Human Follicle Stimulating Hormone: First Proposal for the Amino Acid Sequence of the Hormone-Specific, β Subunit (hFSHβ)", J. Clin. Endocrinol. Metab., vol. 39, 187, pp. 203-205, 1974.

Strickland, Thomas W. et al, "The Kinetic and Equilibrium Parameters of Subunit Association and Gonadotropin Dissociation", The Journal of Biological Chemistry, 1982, vol. 257, No. 6 pp. 2954-2960.

Sugahara, Tadashi et al., "Expression of biologically active fusion genes encoding the common α subunit and either the CGβ or FSHβ subunits: role of a linker sequence", Molecular and Cellular Endocrinology 125 (1996) pp. 71-77.

"The United States Pharmacopeia, Twenty-First Revision", United States Pharmacopeial Convention, Inc., Official from Jan. 1, 1985, prepared by the Committee of Revision and published by the Board of Trustees, pp. 1491-1493, 1984.

Vahl, et al., "Bioavailability of Recombinant Human Growth Hormone in Different Concentrations and Formulations", Pharmacology & Toxicology 79:144-49, 1996.

Voortman, Gerritt et al, "Bioequivalence of subcutaneous injections of recombinant human follicle stimulating hormone (Puregon®) by Pen-injector and syringe", Human Reproduction, 1999, vol. 14, No. 7, pp. 1698-1702.

Wallhausser K-H, "Antimicrobial Preservatives in Europe: Experience with Preservatives Used in Pharmaceuticals and Cosmetics", International Symposium on Preservation in Biological Products, San Francisco 1973, Develop. Biol. Standard, vol. 24, pp. 9-28, 1974.

Anchordoquy, Thomas J. et al., "Polymers Protect Lactate Dehydrogenase during Freeze-Drying by Inhibiting Dissociation in the Frozen State", Archives of Biochemistry and Biophysics, vol. 332, No. 2, Aug. 15, 1996, Article No. 0337, pp. 231-238.

Anik, Shabbir T. et al., "Adsorption of D-Nal(2) [6]LHRH, a decapeptide, onto glass and other surfaces", Institute of Pharmaceutical Sciences, Syntax Research, Palo Alto, CA, International Journal of Pharmaceutics, vol. 16, 1983, pp. 181-190.

Bam, Narendra B. et al. "Stability of Protein Formulations: Investigation of Surfactant Effects by a Novel EPR Spectroscopic Technique", Research Article, Pharmaceutical Research, vol. 12, No. 1, 1995, pp. 2-11.

Baselga, Jose et al., "Phase II Study of Weekly Intravenous Recombinant Humanized Anti-p185[HER2] Monoclonal Antibody in Patients with HER2/neu-Overexpressing Metastic Breast Cancer", Journal of Clinical Oncology, vol. 14, No. 3, Mar. 1996, pp. 737-744.

Boulet, Louis-Philippe et al., "Inhibitory Effects of an Anti-IgE Antibody E25 on Allergen-induced Early Asthmatic Response", Am J Respir Crit Care Med., vol. 155, 1997, pp. 1835-1840.

Butt, W. R., "The Iodination of Follicle-Stimulating and Other Hormones for Radioimmunossay", J. Endocr., 1972, vol. 55, pp. 453-454.

Jentoft, Neil, "Why are proteins O-glycosylated?", TIBS 15, Aug. 1990, Elsevier Sciences Publishers Ltd. (UK), pp. 291-294.

Ketelslegers, J.-M et al., "Receptor Binding Properties of $^{125}$I-hFSH Prepared by Enzymatic Iodinzation", Submitted Aug. 30, 1974, J. Clin. Endocrinol Metabl, vol. 39, No. 6, 1974, pp. 1159-1162.

Kibbe, Arthur H. (Editor), "Benzyl Alcohol", Handbook of Pharmaceutical Excipients, Third Edition, American Pharmaceutical Association, 2000, pp. 41-43.

Marana, R. et al., "Influence of the Purity of the Iodinated Tracer on the Specificity of the Radioimmunoassay of Human Follicle-Stimulating Hormone", Acta Endocrinologica, vol. 92, 1979, pp. 585-598.

Miyachi, Yukitaka, et al., "Structural Integrity of Gonadotropins after Enzymatic Iodination", Biochemical and Biophysical Research Communications, vol. 46, No. 3, 1972, pp. 1213-1221.

Mizutani, Takaharu et al., "Estimation of Adsorption of Drugs and Proteins on Glass Surfaces with Controlled Pore Glass as a Reference", Journal of Pharmaceutical Sciences, vol. 67., No. 8, Aug. 1978, American Pharmaceutical Association, pp. 1102-1105.

Mizutani, Takaharu, et al., "Study of Protein Adsorption on Glass Surfaces with a Hydrophobic Fluorescent Probe", Chem. Pharm. Bulletin, vol. 32, No. 6, 1984, pp. 2395-2400.

Newman et al. "Use of Nonionic Block Copolymers in Vaccines and Therapeutics", Critical Reviews in Therapeutic Drug Carrier Systems, 1998, vol. 15, No. 2, pp. 89-140.

Pikal, Michael J. et al., "The Effects of Formulation Variables on the Stability of Freeze-Dried Human Growth Hormone", Pharmaceutical Research, vol. 8, No. 4, 1991, pp. 427-436.

Pinto, Heidi et al., "Preparation of High-Quality Iodine-125-Labelled Pituitary Human Follicle-Stimulating Hormone (hFSH) for Radioimmunoassay: Comparison of Enzymatic and Chloramine-T Iodination", Clinica Chimica Acta, Elsevier/North-Holland Biomedical Press, vol. 76, 1977, pp. 25-34.

Rathnam, P. et al., "Studies on Modification of Tryptophan, Methionine, Tyrosine and Arginine Residues of Human Follicle-Stimulating Hormone and Its Subunits", Biochimica et Biophysica Acta, vol. 576, 1979, Elsevier/North-Holland Biomedical Press, pp. 81-87.

Silberring, Jerzy et al., "A Universal and Simple Chloramine T Version for Hormone Iodination", International Journal of Applied Radiation and Isotopes, vol. 33, 1982, pp. 117-119.

Stankov, B. M. et al., "The Effect of the Purity of the Iodinated Tracer on the Specificity of a Homologous Assay of Ovine Follicle Stimulating Hormone", Biochemistry International, vol. 12, No. 1, Jan. 1986, pp. 11-19.

Suginami, H. et al., "Influence of the Purity of the Iodinated Tracer on the Specificity of the Radiommunoassay of Human Luteinizing Hormone", Acta Endocrinologica, vol. 89, 1978, pp. 506- 520.

Terada, Shigeyuki, "Iodination of Luteinizing Hormone-Releasing Hormone", Biochemistry 1980, vol. 19, pp. 2572-2576.

"Urofollitropin", European Pharmacopia 2001, 1997:0958 (last revised version of 2001), pp. 1-6.

Van den Steen, Philippe et al., "Concepts and Principles of O-Linked Glycosylation", hCG papers / CTP extensions / Boime papers, Critical Reviews in Biochemistry and Molecular Biology, vol., 35, No. 3, 1998, pp. 151-208.

Wang, Yu-Chang John et al., "Review of Excipients and pH's for Parenteral Products Used in the United States", Journal of the Parenteral Drug Association, vol. 34, No. 6, Nov.-Dec. 1980, pp. 452-462.

Walsh, Gary, "Pharmaceutical biotechnology products approved within the European Union", European Journal of Pharmaceutics and Biopharmaceutics, vol. 55, 2003, pp. 3-10.

Waterman, Kenneth C. et al., "Stabilization of Pharmaceuticals to Oxidative Degradation", Pharmaceutical Development and Technology, vol. 7, No. 1, 2002, pp. 1-32.

Wenzel et al. "Pluronic F127 gel formulations of Deslorelin and GnRH reduce drug degradation and sustain drug release and effect in cattle", Journal of Controlled Release, 2002, vol. 85, pp. 51-59.

Xing, Yongna et al., "Threading of a glycosylated protein loop through a protein hole: Implications for combination of human chorionic gonadotropin subunits", Protein Science, vol. 10, 2001, pp. 226-235.

Burgues et al. "Subcutaneous self-administration of highly purified follicle stimulating hormone and human chorionic gonadotrophin for the treatment of male hypogonadotropic hypogonadism", Human Reproduction, vol. 12, No. 5, pp. 980-986 1997.

Shome et al. "A Reevaluation of the Amino Acid Sequence of Human Follitropin beta-Subunit", Journal of Protein Chemistry, vol. 7, No. 4, pp. 325-339 1988.

Keutmann et al. "Structure of Human Luteinizing Hormone Beta Subunit: Evidence for a Related Carboxyl-Terminal Sequence Among Certain Peptide Hormones", Biochemical and Biophysical Research Communications, vol. 90, No. 3, pp. 842-848 1979.

Talmadge et al. "Evolution of the genes for the beta subunits of human chorionic gonadotropin and luteinizing hormone", Nature, vol. 307, pp. 37-40 1984.

Fiddes et al. "Structure, Expression, and Evolution of the Genes for the Human Glycoprotein Hormones", Recent Progress in Hormone Research, vol. 40, pp. 43-78 1984.

Reichert et al. "Dissociation of Human Follicle-stimulating Hormone", Journal of Biological Chemistry, vol. 250, No. 8, pp. 3034-3040 1975.

Klein et al. "Pharmacokinetics and pharmacodynamics of single-chain recombinant human follicle-stimulating hormone containing the human chorionic gonadotropin carboxyterminal peptide in the rhesus monkey". Fertility and Sterility, vol. 77. No. 6, pp. 1248-1255 2002.

Fiddes et al. "The Gene Encoding the Common Alpha Subunit of the Four Human Glycoprotein Hormones", Journal of Molecular and Applied Genetics, vol. 1. pp. 3-18 1981.

Maurer et al. "Isolation and Nucleotide Sequence Analysis of a Cloned cDNA Encoding the beta-Subunit of Bovine Follicle-Stimulating Hormone", DNA, vol. 5, No. 5, pp. 363-369.

Watkins et al. "DNA Sequence and Regional Assignment of the Human Follicle-Stimulating Hormone beta-Subunit Gene to the Short Arm of Human Chromosome 11", DNA, vol. 6, No. 3, pp. 205-212 1987.

Hirai et al. "The gene for the beta subunit of porcine FSH: absence of consensus oestrogen-responsive element and presence of retroposons", Journal of Molecular Endocrinology, vol. 5, pp. 147-158 1990.

Maurer, "Molecular Cloning and Nudeotide Sequence Analysis of Complementary Deoxyribonucleic Acid for the beta-Subunit of Rat Follicle Stimulating Hormone", Molecular Endocrinology, vol. 1, pp. 717-723 1987.

Guzman et al. "The Gene Encoding Ovine Follicle-Stimulating Hormone beta: Isolation. Characterization, and Comparison to a Related Ovine Genomic Sequence", DNA and Cell Biology, vol. 10, No. 8, pp. 593-601 1991.

Kumar et al. "Cloning of the mouse gonadotropin beta-subunit-encoding genes, II. Structure of the luteinizing hormone beta-subunit-encoding genes", Gene, vol. 166, pp. 335-336 1995.

Kumar et al. "Cloning of the mouse gonadotropin beta-subunit-encoding genes, I. Structure of the follicle-stimulating hormone beta-subunit-encoding gene", Gene, vol. 166, pp. 333-334 1995.

Steelman et al. "Assay of the Follicle Stimulating Hormone Based on the Augmentation with Human Chorionic Gonadotropin", Endocrinology, vol. 53, pp. 604-616 1953.

Van Hell et al. "Effects of Human Menopausal Gonadotrophin Preparations in Different Bioassay Methods", Acta EndocrInologica, vol. 47, pp. 409-418 1964.

U.S. Appl. No. 10/561,529, filed Dec. 20, 2005, Samaritani, et al.

U.S. Appl. No. 10/551,840, filed Oct. 3, 2005, Samaritani, et al.

* cited by examiner

SEQUENCE LISTING

<160> NUMBER OF SEQ ID NOS: 6

<210> SEQ ID NO 1
<211> LENGTH: 91
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Val Glu Asn His Thr Ala
65                  70                  75                  80

Cys His Cys Ser Thr Cys Tyr Tyr His Lys Ser
                85                  90

<210> SEQ ID NO 2
<211> LENGTH: 129
<212> TYPE: PRT
<213> ORGANISM: Homo sapiens

<400> SEQUENCE: 2

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu

<210> SEQ ID NO 3
<211> LENGTH: 108
<212> TYPE: PRT
<213> ORGANISM: Homo sapiens

<400> SEQUENCE: 3

Asn Ser Cys Glu Leu Thr Asn Ile Thr Ile Ala Ile Glu Lys Glu Glu
1               5                   10                  15

```
Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
            85                  90                  95

Arg Gly Leu Gly Pro Ser Tyr Cys Ser Phe Gly Glu
            100                 105

<210> SEQ ID NO 4
<211> LENGTH: 106
<212> TYPE: PRT
<213> ORGANISM: Homo sapiens

<400> SEQUENCE: 4

Asn Ser Cys Glu Leu Thr Asn Ile Ala Ile Glu Lys Glu Glu Cys Arg
 1               5                  10                  15

Phe Cys Ile Ser Ile Asn Thr Trp Cys Ala Gly Tyr Cys Tyr Thr Arg
            20                  25                  30

Asp Leu Val Tyr Lys Asp Pro Ala Arg Pro Lys Ile Gln Lys Thr Cys
            35                  40                  45

Thr Phe Lys Glu Leu Val Tyr Glu Thr Val Arg Val Pro Gly Cys Ala
 50                  55                  60

His His Ala Asp Ser Leu Tyr Thr Val Pro Val Ala Thr Gln Cys His
 65                  70                  75                  80

Cys Gly Lys Cys Asp Ser Asp Ser Thr Asp Cys Thr Val Arg Gly Leu
            85                  90                  95

Gly Pro Ser Tyr Cys Ser Phe Gly Glu Met
            100                 105

<210> SEQ ID NO 5
<211> LENGTH: 110
<212> TYPE: PRT
<213> ORGANISM: Homo sapiens

<400> SEQUENCE: 5

Asn Ser Cys Glu Leu Thr Asn Ile Thr Ile Ala Ile Glu Lys Glu Glu
 1               5                  10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
 65                  70                  75                  80

Gln Cys His Cys Gly Lys Cys Asp Ser Asp Ser Thr Asp Cys Thr Val
            85                  90                  95

Arg Gly Leu Gly Pro Ser Tyr Cys Ser Phe Gly Glu Met Lys
            100                 105                 110

<210> SEQ ID NO 6
```

-continued

```
<211> LENGTH: 112
<212> TYPE: PRT
<213> ORGANISM: Homo sapiens

<400> SEQUENCE: 6

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Arg Val Leu Gln Ala Val Leu
        35                  40                  45

Pro Pro Leu Pro Gln Val Cys Thr Tyr Arg Asp Val Arg Phe Glu Ser
    50                  55                  60

Ile Arg Leu Pro Gly Cys Pro Arg Gly Val Asp Pro Val Val Ser Phe
65                  70                  75                  80

Pro Val Ala Leu Ser Cys Arg Cys Gly Pro Cys Arg Arg Ser Thr Ser
                85                  90                  95

Asp Cys Gly Gly Pro Lys Asp His Pro Leu Thr Cys Asp His Pro Gln
            100                 105                 110
```

FREEZE-DRIED FSH/LH FORMULATIONS

FIELD OF INVENTION

The invention relates to the field of freeze dried formulations of follicle-stimulating hormone (FSH), luteinising hormone (LH), and mixtures of FSH and luteinising hormone (LH), and to methods of producing such formulations.

BACKGROUND OF THE INVENTION

Follicle-stimulating hormone (FSH), luteinising hormone (LH) and chorionic gonadotrophin (CG) are injectable proteins falling into the class of gonadotrophins. FSH, LH and hCG are used alone and in combination in the treatment of infertility and reproductive disorders in both female and male patients.

In nature, FSH and LH are produced by the pituitary gland. For pharmaceutical use, FSH and LH and their variants may be produced recombinantly (rFSH and rLH), or they may be produced from the urine of postmenopausal women (uFSH and uLH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day) for a period of from about 6 to about 12 days.

FSH is also used to induce spermatogenesis in men suffering from oligospermia. A regimen using 150 IU FSH 3 times weekly in combination with 2'500 IU hCG twice weekly has been successful in achieving an improvement in sperm count in men suffering from hypogonadotrophic hypogonadism[1].

LH is used in female patients in combination with FSH in OI and in COH, particularly in those patients having very low endogenous LH levels or resistance to LH, such as women suffering from hypogonadotrophic hypogonadism (HH, WHO group I) or older patients (i.e. 35 years or older), and patients in which embryo implantation or early miscarriage is a problem. LH in combination with FSH has traditionally been available in a preparation called human menopausal gonadotrophins (hMG) extracted from the urine of postmenopausal women. hMG has a 1:1 ratio of FSH:LH activity.

CG acts at the same receptor as LH and elicits the same responses. CG has a longer circulation half-life than LH and is therefore commonly used as a long-acting source of LH-activity. CG is used in OI and COH regimens to mimic the natural LH peak and trigger ovulation. An injection of human chorionic gonadotrophin (hCG) is used to trigger ovulation at the end of stimulation with FSH or a mixture of FSH and LH. CG may also be used together with FSH during stimulation for OI and COH, in order to provide LH-activity during stimulation in patients in which LH-activity is desirable, such as those mentioned above.

FSH, LH and CG are members of the heterodimer, glycoprotein hormone family that also includes thyroid stimulating hormone (TSH). The members of this family are heterodimers, comprising an α- and a β-subunit. The subunits are held together by noncovalent interactions. The human FSH (hFSH) heterodimer consists of (i) a mature 92 amino acid glycoprotein alpha subunit, which also is common to the other human family members (i.e., chorionic gonadotrophin ("CG"), luteinising hormone ("LH") and thyroid stimulating hormone ("TSH"); and (ii) a mature 111 amino acid beta subunit that is unique to FSH[2]. The human LH heterodimer consists of (i) the mature 92 amino acid glycoprotein alpha subunit; and (ii) a mature 112 beta subunit that is unique to LH[3]. The alpha and beta subunits of the glycoproteins may be prone to dissociate in formulations, due to interaction with a preservative, surfactant and other excipients. Dissociation of the subunits leads to loss of biological potency[4].

FSH is formulated for intramuscular (IM) or subcutaneous (SC) injection. FSH is supplied in lyophilised (solid) form in vials or ampoules of 75 IU/vial and 150 IU/vial with a shelf life of one and a half to two years when stored at 2-25° C. A solution for injection is formed by reconstituting the lyophilised product with water for injection (WFI). For ovulation induction or controlled ovarian hyperstimulation, daily injections with starting doses of 75 IU to 600 IU are recommended for up to about ten days. Depending on the patient's response, up to three cycles of treatment with increasing doses of FSH can be used. With lyophilised formulations, the patient is required to reconstitute a new vial of lyophilised material with diluent and administer it immediately after reconstitution on a daily basis [Package Insert N1700101A, published in February 1996, for Fertinex™ (urofollitropin for injection, purified) for subcutaneous injection, by Serono Laboratories, Inc., Randolph, Mass.].

FSH has also been formulated in both single-dose and multi-dose liquid formats, in vials, or ampoules. Single dose formats must remain stable and potent in storage prior to use. Multi-dose formats must not only remain stable and potent in storage prior to use, but must also remain stable, potent and relatively free of bacteria over the multiple-dose use regimen administration period, after the seal of the ampoule has been compromised. For this reason, multi-dose formats contain a bacteriostatic agent.

LH is formulated for intramuscular (IM) or subcutaneous (SC) injection. LH is supplied in lyophilised (solid) form in vials or ampoules of 75 IU/vial with a shelf life of one and a half to two years when stored at 2-25° C. A solution for injection is formed by reconstituting the lyophilised product with water for injection (WFI). For ovulation induction or controlled ovarian hyperstimulation, in conjunction with FSH, daily injections with starting doses of 75 IU to 600 IU LH are recommended for up to about ten days.

EP 0 618 808 (Applied Research Systems ARS Holding N.V.) discloses a pharmaceutical composition comprising a solid intimate mixture of gonadotrophin and a stabilising amount of sucrose alone or in combination with glycine.

EP 0 814 841 (Applied Research Systems ARS Holding N.V.) discloses a stable, liquid pharmaceutical composition comprising recombinant human chorionic gonadotrophin (hCG) and a stabilizing amount of mannitol.

EP 0 448 146 (AKZO N.V.) discloses a stabilized gonadotrophin containing lyophilisate comprising one part by weight of a gonadotrophin; and 200 to 10,000 parts by weight of a dicarboxylic acid salt stabilizer associated with the gonadotrophin.

EP 0 853 945 (Akzo Nobel N.V.) discloses a liquid gonadotrophin-containing formulation characterised in that the formulation comprises a gonadotrophin and stabilising amounts of a polycarboxylic acid or a salt thereof and of a thioether compound.

WO 00/04913 (Eli Lilly and Co.) discloses a formulation comprising FSH or an FSH variant, containing an alpha and beta subunit, and a preservative selected from the group consisting of phenol, m-cresol, p-cresol, o-cresol, chlorocresol, benzyl alcohol, alkylparaben (methyl, ethyl, propyl, butyl and the like), benzalkonim chloride, benzethonium chloride, sodium dehydroacetate and thimerosal, or mixtures thereof in an aqueous diluent.

SUMMARY OF THE INVENTION

It is an object of the invention to provide new freeze dried formulations of mixtures of FSH and LH, to provide methods for their preparation, and methods for their pharmaceutical or veterinary use in the treatment of fertility disorders.

In a first aspect, the invention provides a freeze dried formulation comprising FSH or a variant thereof as well as LH or a variant thereof, and a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate).

In a second aspect, the invention provides a method for manufacturing a freeze dried formulation comprising forming a mixture of FSH or a variant thereof and LH or a variant thereof with a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate) and subjecting the mixture to lyophillsation.

In an third aspect, the invention provides an article of manufacture for human pharmaceutical use, comprising a first container comprising freeze dried FSH as well as LH or an FSH or LH variant, and a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate) and a second container comprising a solvent for reconstitution.

DETAILED DESCRIPTION OF THE INVENTION

The mixed FSH/LH formulations of the present invention have improved or more suitable properties or stability, and are useful for infertility treatment in women and/or men. These formulations and articles of manufacture are additionally suitable for use in injectable and alternative delivery systems, e.g., but not limited to, nasal, pulmonary, transmucosal, transdermal, oral, subcutaneous, intramuscular or parenteral sustained release. In a particularly preferred embodiment the formulations of the invention are for subcutaneous and/or intramuscular injection. The FSH, LH or FSH and LH variant formulations provided may also have increased in vivo potency over time compared to known commercial products, by preventing or reducing loss of activity or stability, or by improving any aspect of the effectiveness or desirability of administration, e.g., by at least one of mode, frequency, dosage, comfort, ease of use, biological activity in vitro or in vivo, and the like.

Follicle stimulating hormone, or FSH, as used herein refers to the FSH produced as a full-length mature protein which includes, but is not limited to human FSH or "hFSH", whether produced recombinantly or isolated from human sources, such as the urine of postmenopausal women. The protein sequence of the human glycoprotein alpha subunit is provided in SEQ ID NO: 1, and the protein sequence of the human FSH beta subunit is given in SEQ ID NO: 2.

The expression "FSH variant" is meant to encompass those molecules differing in amino acid sequence, glycosylation pattern or in inter-subunit linkage from human FSH but exhibiting FSH-activity. Examples include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al; Endocrinology; 1992, 131, 2514-2520; or Klein et al.; Development and characterization of a long-acting recombinant hFSH agonist; Human Reprod. 2003, 18, 50-56]. Also included is single chain CTP-FSH, a single chain molecule, consisting of the following sequences (from N-terminal to C-terminal):

| βFSH | βhCG-CTP(113-145) | αFSH |
|------|-------------------|------| wherein βFSH signifies the β-subunit of FSH, βhCG CTP (113-145) signifies the carboxy terminal peptide of hCG and αFSH signifies the α-subunit of FSH, as described by Klein et al[5]. Other examples of FSH variants include FSH molecules having additional glycosylation sites incorporated in the α- and/or β-subunit, as disclosed in WO 01/58493 (Maxygen), particularly as disclosed in claims 10 and 11 of WO 01/58493, and FSH molecules with intersubunit S—S bonds, as disclosed in WO 98/58957.

The FSH variants referred to herein also include the carboxy terminal deletions of the beta subunit that are shorter than the full length mature protein of SEQ ID NO:2. Carboxy terminal deletions of the human beta subunit are provided in SEQ IDS NOS: 3, 4, and 5. It is understood that the carboxy terminal variants of the beta chain form dimers with a known alpha subunit to form an FSH variant heterodimer.

FSH heterodimers or FSH variant heterodimers can be produced by any suitable method, such as recombinantly, by isolation or purification from natural sources as may be the case, or by chemical synthesis, or any combination thereof.

The use of the term "recombinant" refers to preparations of FSH, LH or FSH and LH variants that are produced through the use of recombinant DNA technology (see for example WO 85/01958). The sequences for genomic and cDNA clones of FSH are known for the alpha and beta subunits of several species[6]. One example of a method of expressing FSH or LH using recombinant technology is by transfection of eukaryotic cells with the DNA sequences encoding an alpha and beta subunit of FSH or LH, whether provided on one vector or on two vectors with each subunit having a separate promoter, as described in European patent nos. EP 0 211 894 and EP 0 487 512. Another example of the use of recombinant technology to produce FSH or LH is by the use of homologous recombination to insert a heterologous regulatory segment in operative connection to endogenous sequences encoding the subunits of FSH or LH, as described in European patent no. EP 0 505 500 (Applied Research Systems ARS Holding NV).

The FSH or FSH variant used in accordance with the present invention may be produced not only by recombinant means, including from mammalian cells, but also may be purified from other biological sources, such as from urinary sources. Acceptable methodologies include those described in Hakola, K. Molecular and Cellular Endocrinology, 127:59-69, 1997; Keene, et al., J. Biol. Chem., 264-4769-4775, 1989; Cerpa-Poljak, et al., Endocrinology, 132:351-356, 1993; Dias, et al., J. Biol. Chem., 269:25289-25294, 1994; Flack, et al., J. Biol. Chem., 269:14015-14020, 1994; and Valove, et al., Endocrinology, 135:2657-2661, 1994, U.S. Pat. No. 3,119,740 and U.S. Pat. No. 5,767,067.

Luteinising hormone, or LH, as used herein refers to the LH produced as a full-length mature protein, which includes, but is not limited to human LH or "hLH", whether produced recombinantly or isolated from human sources, such as the urine of postmenopausal women. The protein sequence of the human glycoprotein alpha subunit is provided in SEQ ID NO:

1, and the protein sequence of the human LH beta subunit[7] is given in SEQ ID NO: 6. In a preferred embodiment the LH is recombinant.

The expression "LH variant" is meant to encompass those molecules differing in amino acid sequence, glycosylation pattern or in inter-subunit linkage from human LH but exhibiting LH-activity.

LH heterodimers or LH variant heterodimers can be produced by any suitable method, such as recombinantly, by isolation or purification from natural sources as may be the case, or by chemical synthesis, or any combination thereof.

The term "administer" or "administering" means to introduce a formulation of the present invention into the body of a patient in need thereof to treat a disease or condition.

The term "patient" means a mammal that is treated for a disease or condition. Patients are of, but not limited to, the following origin, human, ovine, porcine, equine, bovine, rabbit and the like.

The term "potency" in relation to FSH activity, refers to the ability of an FSH formulation or a mixed formulation, to elicit biological responses associated with FSH, such as ovarian weight gain in the Steelman-Pohley assay[8], or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

The term "potency" in relation to LH activity, refers to the ability of an LH formulation or a mixed formulation, to elicit biological responses associated with LH, such as seminal vesicle weight gain method.[9] Biological activity of LH is evaluated with respect to an accepted standard for LH.

The term "aqueous diluent" refers to a liquid solvent that contains water. Aqueous solvent systems may be consist solely of water, or may consist of water plus one or more miscible solvents, and may contain dissolved solutes such as sugars, buffers, salts or other excipients. The more commonly used non-aqueous solvents are the short-chain organic alcohols, such as, methanol, ethanol, propanol, short-chain ketones, such as acetone, and poly alcohols, such as glycerol.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g., glycine or albumin), salts (e.g., sodium chloride), and sugars (e.g., dextrose, sucrose and lactose).

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are phosphate buffers with saline or an acceptable salt.

The term "phosphate buffer" refers to solutions containing phosphoric acid or salts thereof, adjusted to a desired pH. Generally phosphate buffers are prepared from phosphoric acid, or a salt of phosphoric acid, including but not limited to sodium and potassium salts. Several salts of phosphoric acid are known in the art, such as sodium and potassium monobasic, dibasic, and tribasic salts of the acid. Salts of phosphoric acid are also known to occur as hydrates of the occurring salt. Phosphate buffers may cover a range of pHs, such as from about pH 4 to about pH 10, and preferred ranges from about pH 5 to about pH 9, and a most preferred range of at or about 6.0 to at or about 8.0, most preferably at or about pH 7.0.

The term "vial" or "container" refers broadly to a reservoir suitable for retaining FSH in solid or liquid form in a contained sterile state. Examples of a vial as used herein include ampoules, cartridges, blister packages, or other such reservoir suitable for delivery of the FSH to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "stability" refers to the physical, chemical, and conformational stability of FSH and LH in the formulations of the present invention (including maintenance of biological potency). Instability of a protein formulation may be caused by chemical degradation or aggregation of the protein molecules to form higher order polymers, by dissociation of the heterodimers into monomers, deglycosylation, modification of glycosylation, oxidation (particularly of the α-subunit) or any other structural modification that reduces at least one biological activity of an FSH polypeptide included in the present invention.

A "stable" solution or formulation, is one wherein the degree of degradation, modification, aggregation, loss of biological activity and the like, of proteins therein is acceptably controlled, and does not increase unacceptably with time. Preferably the formulation retains at least at or about 80% of the labelled FSH activity and at least at or about 80% of the labelled LH activity over a period of 6 months at a temperature of at or about 2-8° C., more preferably at or about 2-8° C., more preferably at or about 4-5° C. FSH activity can be measured using the Steelman-Pohley ovarian weight gain bioassay[5]. LH activity can be measured using the seminal vesicle weight gain bioassay[10].

The term "treating" refers to the administration, follow up, management and/or care of a patient for which FSH and/or LH administration is desirable for the purpose of follicle or testicular stimulation or any other physiological response regulated by FSH and/or LH. Treating can thus include, but is not limited to, the administration of FSH and/or LH for the induction or improvement of sperm quality, stimulation of testosterone release in the male, or follicular development or for ovulation induction in the female.

A "salt" of a protein is an acid or base addition salt. Such salts are preferably formed between any one or more of the charged groups in the protein and any one or more physiologically acceptable, non-toxic cations or anions. Organic and inorganic salts include, for example, those prepared from acids such as hydrochloric, sulphuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

The inventors have found that a surfactant selected from the group of polysorbates, in particular Tween 20 (polyoxyethylene (20) sorbitan monolaurate), Tween 40 (polyoxyethylene (20) sorbitan monopalmitate), Tween 80 (polyoxyethylene (20) sorbitan monooleate) is a suitable excipient for preparing a stable formulation comprising a mixture of LH and FSH. The preferred surfactant is Tween 20. Polysorbates are surfactants which are commercially available (e.g. from Merck).

The surfactant, e.g. Tween 20, is preferably present in the freeze dried formulation at a concentration of at or about 0.001 to at or about 0.1 mg per mg of the total formulation, more preferably at or about 0.01 to at or about 0.075 mg/mg.

Preferably the concentration of Tween, particularly Tween 20, in the reconstituted formulations is at or about 0.01 mg/ml to at or about 1 mg/ml, more preferably at or about 0.05 mg/ml to at or about 0.5 mg/ml, more particularly preferably at or about 0.2 mg/ml to at or about 0.4 mg/ml, most preferably at or about 0.1 mg/ml.

The follicle-stimulating hormone (FSH) within the freeze-dried formulation is preferably present at a concentration (w/w) of at or about 0.1 to 10 µg/mg of the total formulation. In one embodiment, the follicle-stimulating hormone (FSH) is present at a concentration of at or about 0.3 to 5 µg/mg of the total formulation. In a further embodiment the follicle-stimulating hormone (FSH) is present at a concentration of at or about 0.37 to 2 µg/mg of the total formulation.

The luteinising hormone (LH) within the freeze-dried formulation is preferably present at a concentration of at or about 0.1 to 3 µg/mg of the total formulation. In one embodiment, the luteinising hormone (LH) is present at a concentration of at or about 0.1 to 1 µg/mg of the total formulation. In a further embodiment, the luteinising hormone (LH) is present at a concentration of at or about 0.1 to 0.6 µg/mg of the total formulation.

In the reconstituted formulations, the concentration of FSH in the formulation preferably is at or about 150 IU/ml to at or about 2,000 IU/ml, more preferably at or about 300 IU/ml to at or about 1,500 IU/ml, more particularly preferably at or about 450 to at or about 750, most preferably at or about 600 IU/ml.

In the reconstituted formulations, the LH concentration in the formulation is preferably at or about 50 IU/ml to at or about 2,000 IU/ml, more preferably at or about 150 to at or about 1,500 IU/ml, more particularly preferably at or about 300 IU/ml to at or about 750 IU/ml, particularly preferably 625 IU/ml.

The ratio of FSH to LH (FSH:LH, IU:IU, FSH measured with rat ovarian weight gain assay and LH measured with rat seminal vesicle weight gain assay) is preferably within the range of at or about 6:1 to at or about 1:6, more preferably at or about 4:1 to at or about 1:2, more particularly preferably at or about 3:1 to at or about 1:1. Particularly preferred ratios are 1:1 and 2:1.

Preferably the FSH and LH are produced recombinantly, particularly preferably they are produced in Chinese hamster ovary cells transfected with a vector or vectors comprising DNA coding for the human glycoprotein alpha-subunit and the beta-subunit of FSH or LH. DNA encoding the alpha and beta-subunits may be present on the same or different vectors.

Recombinant FSH and LH have several advantages over their urinary counterparts. Culture and isolation techniques using recombinant cells permit consistency between batches. In contrast, urinary FSH and LH vary greatly from batch to batch in such characteristics as purity, glycosylation pattern, sialylation and oxidation of the subunits. Due to greater batch-to-batch consistency and purity of recombinant FSH and LH, the hormones can be readily identified and quantified using techniques such as isoelectric focussing (IEF). The ease with which recombinant FSH and LH can be identified and quantified permits the filling of vials by mass of hormone (fill-by-mass) rather than filling by bioassay.

Preferably the freeze dried formulations of the present invention have a buffer, preferably a phosphate buffer, with preferred counterions being sodium or potassium ions. Phosphate saline buffers are well known in the art, such as Dulbecco's Phosphate buffered saline. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 10 mM in phosphate ions with a pH of 7.0.

Preferably the buffer is adjusted in such a way that the reconstituted formulations of the freeze dried formulations of the present invention have a pH between at or about 6.0 and at or about 8.0, more preferably at or about 6.8 to at or about 7.8, including about pH 7.0, pH 7.2, and 7.4.

Preferably the buffer is adjusted in such a way that the reconstituted formulations of mixtures of FSH and LH of the present invention have pH between at or about 6.0 and at or about 9.0, more preferably at or about 6.8 to at or about 8.5, including about pH 7.0, pH 8.0, and 8.2, most preferably at or about pH 8.0.

In order to provide for an injectable, the freeze dried formulations of the present invention are reconstituted using a suitable solvent. A preferred solvent is water for injection.

In a further specific embodiment, the invention provides a freeze dried formulation, comprising FSH and LH, a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate). Preferably the FSH and LH are present in a ratio (FSH:LH) of at or about 2:1 to at or about 1:1.

In a further specific embodiment, the invention provides a method for manufacturing a freeze dried formulation, comprising forming a mixture of FSH and LH as well as a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate), and subjecting said mixture to lyophilisation.

In yet another preferred embodiment, the invention provides a method for manufacturing a packaged pharmaceutical composition comprising dispensing a freeze dried mixture comprising FSH as well as LH and a surfactant selected from Tween 20 (polyoxyethylene (20) sorbitan monolaurate), Tween 40 (polyoxyethylene 20) sorbitan monopalmitate), Tween 80 (polyoxyethylene (20) sorbitan monooleate) into a container.

In yet another preferred embodiment, the invention provides an article of manufacture for human pharmaceutical use, comprising a first container or vial comprising freeze dried FSH or an FSH variant as well as LH or an LH variant and a surfactant selected from Tween 20 (polyoxyethylene (20) sorbitan monolaurate), Tween 40 (polyoxyethylene (20) sorbitan monopalmitate), Tween 80 (polyoxyethylene (20) sorbitan monooleate). A second container or vial contains a diluent for reconstitution, preferably water.

The freeze dried formulations of the invention may be kept for at least at or about 6 months, 12 months or 24 months. Under preferred storage conditions, before the first use, the formulations are kept away from bright light (preferably in the dark), at temperatures of at or about 25, preferably of at or about 2-8° C., more preferably at or about 4-5° C.

Preferably the freeze dried formulations of the invention contain an antioxidant, such as methionine, sodium bisulfite, salts of ethylenediaminetetraacetic acid (EDTA), butylated hydroxytoluene (BHT), and butylated hydroxy anisole (BHA). Most preferred is methionine. The antioxidant prevents oxidation of FSH and LH (particularly the α-subunit).

The antioxidant, e.g. methionine is preferably present at a concentration of at or about 0.001 to at or about 0.1 mg per mg of total formulation, more preferably at or about 0.01 to at or about 0.075 mg/mg.

In the reconstituted formulation, methionine is preferably present at a concentration of at or about 0.01 to at or about 1.0 mg/ml, more preferably at or about 0.05 to at or about 0.5 mg/ml, most preferably at or about 0.1 mg/ml.

Preferably the freeze dried formulations formulations of the invention contain a mono- or disaccharide or a sugar alcohol as stabiliser and tonicity adjusting agent, such as sucrose, dextrose, lactose, mannitol and/or glycerol. Most preferred is sucrose. In the reconstituted formulation, sucrose is present at or about 60 mg/ml.

As noted above, the invention provides freeze dried formulations in particular for single use. The formulations of the invention are suitable for pharmaceutical or veterinary use.

As noted above, in a preferred embodiment, the invention provides an article of manufacture, comprising packaging material and a vial comprising freeze dried FSH and LH as well as Tween 20. The second container includes water for injection as diluent.

The range of protein hormone in the formulations of the invention includes amounts yielding upon reconstitution, concentrations from about 1.0 µg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The protein hormone concentration is preferably at or about 5.0 µg/ml to at or about 2 mg/ml, more preferably at or about 10 µg/ml to at or about 1 mg/ml, most preferably at or about 50 µg/ml to at or about 200 µg/ml.

Preferably the formulations of the invention retain at least at or about 80% of the FSH activity and/or LH activity at the time of packaging over a period of 24 months (before the first use). FSH activity can be measured using the Steelman-Pohley ovarian weight gain bioassay[5]. LH activity can be measured using the rat seminal vesicle weight gain bioassay.

The formulations of the present invention can be prepared by a process which comprises mixing FSH and LH and Tween 20 as well as further excipients like an antioxidant and/or a buffer and subjecting the mixture to a lyophilisation. Mixing the components and lyophilising them is carried out using conventional procedures. To prepare a suitable formulation, for example, a measured amount of FSH or FSH variant, LH or LH variant is combined with Tween 20 and the resulting mixture is lyophilized and then dispensed into vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

The reconstituted formulations obtained from the freeze dried formulations of the invention can be administered using recognized devices. Examples comprising these single vial systems include pen-injector devices for delivery of a solution such as EasyJect®, Gonal-F® Pen, Humaject®, NovoPen®, B-D®Pen, AutoPen®, and OptiPen®.

The products presently claimed include packaging material. The packaging material provides, in addition to the information required by the regulatory agencies, the conditions under which the product may be used. The packaging material of the present invention provides instructions to the patient to reconstitute the freeze dried formulation of the invention in the aqueous diluent to form a solution and to use the solution over a period of twenty-four hours or greater for the two vial, wet/dry, product. For the single vial, solution product, the label indicates that such solution may be stored after first use for a period of twenty-four hours or greater, preferably for up to 12 or 14 days. The presently claimed products are useful for human pharmaceutical product use.

The following example is provided merely to further illustrate the preparation of the formulations and compositions of the invention. The scope of the invention shall not be construed as merely consisting of the following example.

Example

The recombinant gonadotropins (FSH/LH) of the present examples have been prepared by expression in CHO (Chinese Hamster Ovary) cells, transformed with the corresponding recombinant DNA, according to the technique described in European patents EP 160699 and EP 211894.

The other substances used in the examples are the following:
Sucrose extra pure Merck code 1.07653
Sodium dihydrogen phosphate monohydrate (following indicated as $NaH_2PO_4\ H_2O$) Merck code 1.06346
Di-Sodium hydrogen phosphate dihydrate (following indicated as $Na_2HPO_4\ 2H_2O$) Merck code 1.06580
Tween 20 Merck code 822184
L-Methionine Rexim
Water for injection
Ortho Phosphoric Acid 85% extra pure Merck code 1.00563
Ortho Phosphoric acid (17% w/w approx.) solution
Sodium Hydroxide pellets extra pure Merck code 1.06498

FSH and LH Freeze Dried Formulation

A freeze dried formulation A having the following composition has been prepared:

| Formulation A | |
|---|---|
| FSH | µg 12.0 (165 I.U.) |
| LH | µg 3.7 (92 I.U.) |
| Sucrose | mg 30.0 |
| $NaH_2PO_4H_2O$ | mg 0.45 |
| $Na_2HPO_42H_2O$ | mg 1.11 |
| Tween 20 | mg 0.05 |
| L-Methionine | mg 0.1 |

The manufacturing process consists in mixing the drug substance directly with the ingredients, filtrating the solution obtained and lyophilising the filtrated.

A description of each step of the process is given in the following:
add in a tared container WFI, di-sodium hydrogen phosphate dihydrate, sodium dihydrogen phosphate monohydrate, Sucrose, Tween 20 at 5% and L-methionine and stir for 10 minutes until complete dissolution.
check the pH and eventually correct it to pH 7.00±0.2 with NaOH 10% or diluted $H_3PO_4$
add FSH and LH to the above prepared mixture and gently stir the solution obtained for 10 minutes.
check the pH again and eventually adjust it to 7.0±0.1 with 10% NaOH or diluted $H_3PO_4$.
filter the solution with a 0.22 µm Durapore membrane with a filtration ratio not less than 15 g/cm2, under Nitrogen gas flow with a pressure not higher than 1.5 atm.
collect the solution in a previously sterilised flask.

fill the filtered solution into the glass container, seat the stopper and place the filled vials into a stainless steel tray.

load the trays into the freeze dryer and lyophilise the product using the following freeze drying cycle:
  equilibrate at +4° C. for about 20 mins.
  bring the shelves temperature at −25° C. and maintain for 2 hours.
  bring the shelves temperature at −15° C. and maintain for 1 hour.
  bring the shelves temperature at −45° C. and maintain for 3 hours.
  bring condenser temperature at −65° C.
  apply vacuum to the chamber.
  When the vacuum reaches a value of $7\times10^{-2}$ mBar raise shelf temperature up to −10° C. and maintain for 14 hours.
  raise the shelf temperature up to +35° C. in 8 hours and maintain up to the end of the cycle (14 hours).
  break the vacuum allowing dry nitrogen into the chamber.
  perform the stoppering by automatic system of the freeze dryer.
  seal the stoppered vials with the appropriate flip-off caps.

The formulations A and B have been stored at 25±2° C., and tested for stability and biological activity as pointed out below. Prior to analysing the compositions, they are reconstituted using water for injection.

The stability and biological activity values were determined as follows:

In vivo assay for FSH: The formulation was tested for FSH activity using the Steelman-Pohley ovarian weight gain bioassay.

In vivo assay for LH: The formulation was tested for LH activity using the rat seminal vesicle weight gain bioassay.

Assay of oxidised alpha-subunit: The percentage of oxidised alpha-subunit was measured by a reverse phase HPLC (RP-HPLC) method.

Evaluation of free subunit (rFSH+rLH): The percentage of free subunit was evaluated by SDS-PAGE.

Evaluation of aggregates: The percentage of aggregates was evaluated by SDS-PAGE as described above for evaluation of free subunit.

The biological tests have been performed in compliance with the regulations of the European Pharmacopeia. In particular the tests are reported in the "Menotropin" monography.

Table 1 summarizes the results of the analytical tests related to stability and biological activity of formulation A. The values were determined at 4 check-points: at time zero, after 1 month, 3 months and 6 months of storage, at a storage temperature of 25±2° C.

TABLE 1

| TEST | TIME ZERO | 1 MONTH | 3 MONTHS | 6 MONTHS |
|---|---|---|---|---|
| Biological activity I.U. FSH | 154 | 136 | 133 | 154 |
| Biological activity I.U. LH | 93 | 86 | 94 | 80 |
| % oxidised product | 1.0 | 1.2 | 2.0 | 1.0 |
| % dimers/aggregates | <2 | <2 | <2 | <2 |
| % free subunits | <5 | <5 | <5 | <5 |

In Table 2 the results of the analytical test related to stability and biological activity on the formulation A stored at 40±2° C. are summarised for 4 check-points: at time zero, after 3 month, 6 months and 9 months of storage.

TABLE 2

| TEST | TIME ZERO | 3 MONTHS | 6 MONTHS | 9 MONTHS |
|---|---|---|---|---|
| Biological activity I.U. FSH | 154 | 139 | 157 | 146 |
| Biological activity I.U. LH | 93 | 102 | 88 | 92 |
| % oxidised product | 1.0 | 0.9 | 1.0 | 1.0 |
| % dimers/aggregates | <2 | <2 | <2 | <2 |
| % free subunits | <5 | <5 | <5 | <5 |

From TABLE 1 and 2 it may be concluded that the biological activity of formulation A is well conserved after 9 months of storage. The formulation has a high stability.

Sequences:
SEQ ID NO. 1: human glycoprotein α-subunit;
SEQ ID NO. 2: hFSH β-subunit
SEQ ID NO. 3: hFSH β-subunit variant 1
SEQ ID NO. 4: hFSH β-subunit variant 2
SEQ ID NO. 5: hFSH β-subunit variant 3
SEQ ID NO. 6: hLH β-subunit

REFERENCES

[1] Burgues et al.; *Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism Hum. Reprod.;* 1997, 12, 980-6;

[2] Shome et al., J. Clin. Endocrinol. Metab. 39:187-205 (1974); Shome, et al., J. Prot. Chem, 7:325-339, 1988;

[3] Keutmann et al; *Structure of human luteinizing hormone beta subunit evidence for related carboxyl-terminal sequence among certain peptide hormones; Biochem. Biophys. Res. Commun.;* 1979, 90, 842-848; Talmadge et al.; *Evolution of the genes for the beta subunits of human chorionic gonadotropin and luteinizing hormone; Nature;* 1984, 307, 37-40; Fiddes & Talmadge; *Structure, expression, and evolution of the genes for the human glycoprotein hormones; Recent Prog. Horm. Res.;* 1984, 40, 43-78

[4] Reichert L E, Ramsey R B; Dissociation of human follicle-stimulating hormone; J. Biol. Chem.; 1975, 250, 3034-3040

[5] Klein et al.; *Pharmacokinetics and pharmacodynamics of single-chain recombinant human follicle-stimulating hormone containing the human chorionic gonadotropin carboxyterminal peptide in the rhesus monkey; Fertility & Sterility;* 2002, 77, 1248-1255

[6] a) Fiddes, J. C., et al., J. of Mol. and Applied Genetics, 1:3-18(1981); b) Esch F. S., et al. DNA 5:363-369(1986); c) Watkins P. C., et al., DNA 6:205-212(1987); d) Hirai T., et al., J. Mol. Endocrinol. 5:147-158(1990): e) Maurer, R. A., et al., Mol. Endocrinol. 1:717-723(1987); f) Guzman K., et al., DNA Cell Biol. 10:593-601(1991); g) Kumar T R, et al., Gene. 1995 Dec. 12; 166(2):335-6; h) Kumar T R, et al., Gene. 1995 Dec 12; 166(2):333-4

[7] Biochem. Biophys. Res. Commun.; 1979, 90, 842-848

[8] Steelman et al.; Assay of the follicle stimulating hormone based on the augmentation with human chorionic gonadotrophin; Endocrinology; 1953, 53, 604-616

The invention claimed is:

1. A freeze-dried formulation consisting of:
a follicle-stimulating hormone or a variant thereof, a luteinising hormone or a variant thereof, at least one surfactant selected from the group consisting of polyoxyethylene (20) sorbitan monolaurate, polyoxyethylene (20) sorbitan monopalmitate, and polyoxyethylene (20) sorbitan monooleate, a stabilizer and tonicity agent selected from the group consisting of monosaccharides, disaccharides and sugar alcohols, methionine, and a phosphate buffer.

2. The freeze-dried formulation of claim 1 consisting of recombinant human follicle-stimulating hormone, recombinant human luteinising hormone, polyoxyethylene (20) sorbitan monolaurate, sucrose, methionine, and a phosphate-buffer.

3. The freeze-dried formulation according to claim 2 including: 0.1-10 µg/mg recombinant human follicle-stimulating hormone, 0.1-3 µg/mg recombinant human luteinising hormone, and 0.001-0.1 mg/mg polyoxyethylene (20) sorbitan monolaurate, based on the weight of the formulation.

4. The freeze-dried formulation according to claim 3 in which the relative weight amounts of the components comprise 12.0 µg of recombinant human follicle-stimulating hormone, 3.7 µg of recombinant human luteinising hormone, 30.0 mg of sucrose, 0.05 mg of polyoxyethylene (20) sorbitan monolaurate and 0.1 mg of methionine.

5. An article of manufacture comprising:
a first container filled with a freeze-dried formulation consisting of a recombinant, human follicle-stimulating hormone or a variant thereof, a recombinant, human luteinising hormone or a variant thereof, polyoxyethylene (20) sorbitan monolaurate, sucrose, methionine; and a phosphate buffer; and
a second container that comprises a solvent for reconstitution.

6. The article of manufacture according to claim 5, wherein the second container contains water for reconstitution.

7. A method for manufacturing a freeze-dried formulation comprising:

forming a mixture consisting of a follicle-stimulating hormone or a variant thereof, a luteinising hormone or a variant thereof, at least one surfactant selected from the group consisting of polyoxyethylene (20) sorbitan monolaurate, polyoxyethylene (20) sorbitan monopalmitate, and polyoxyethylene (20) sorbitan monooleate, a stabilizer and tonicity agent selected from the group consisting of monosaccharides, disaccharides and sugar alcohols, methionine, and a phosphate buffer; and
subjecting the mixture to lyophilization.

8. The method according to claim 7, wherein the mixture consists of recombinant human follicle-stimulating hormone, recombinant human luteinising hormone, sucrose, polyoxyethylene (20) sorbitan monolaurate and methionine.

9. The method according to claim 8, wherein the mixture consists of component amounts to yield a freeze-dried formulation containing 0.1-10 µg/mg recombinant human follicle-stimulating hormone, 0.1-3 µg/mg recombinant human luteinising hormone, and 0.001-0.1 mg/mg polyoxyethylene (20) sorbitan monolaurate, based on the weight of the formulation.

10. The method according to claim 9, wherein the mixture consists of component amounts to yield relative weight amounts of the components in the freeze-dried formulation comprising 12.0 µg of recombinant human follicle-stimulating hormone, 3.7 µg of recombinant human luteinising hormone, 30.0 mg of sucrose, 0.05 mg of polyoxyethylene (20) sorbitan monolaurate and 0.1 mg of methionine.

11. The article of manufacture of claim 5 in which the first container is filled with a freeze-dried formulation consisting of recombinant human follicle-stimulating hormone, recombinant human luteinising hormone, polyoxyethylene (20) sorbitan monolaurate, sucrose, methionine, and a phosphate-buffer.

12. The freeze-dried formulation of claim 1 in which the biological activity of the FSH and of the LH is well conserved after nine months of storage.

* * * * *